United States Patent [19]

Wudl et al.

[11] Patent Number: 4,626,586

[45] Date of Patent: Dec. 2, 1986

[54] TRANSITION METAL POLY(BENZODITHIOLENE)

[75] Inventors: Fred Wudl; Alan J. Heeger, both of Santa Barbara, Calif.; Carl W. Dirk, Piscataway, N.J.

[73] Assignee: Regents of the University of California, Berkeley, Calif.

[21] Appl. No.: 765,303

[22] Filed: Aug. 13, 1985

[51] Int. Cl.[4] ............................................. C08G 75/14
[52] U.S. Cl. ..................................... 528/374; 528/395
[58] Field of Search ................................ 528/374, 395

[56] References Cited

U.S. PATENT DOCUMENTS

| | | | |
|---|---|---|---|
| 3,294,761 | 12/1966 | Warner | 528/374 |
| 3,402,134 | 9/1968 | Berenbaum et al. | 528/374 |
| 3,607,845 | 9/1971 | Ireland et al. | 528/374 |

*Primary Examiner*—Harold D. Anderson
*Attorney, Agent, or Firm*—Nilsson, Robbins, Dalgarn, Berliner, Carson & Wurst

[57] ABSTRACT

Poly(benzodithiolenes) containing transition metals having desirable chemical, physical, electrical and magnetic properties are prepared by reacting an aromatic tetrathiol with a transition metal salt.

24 Claims, No Drawings

TRANSITION METAL POLY(BENZODITHIOLENE)

BACKGROUND OF THE INVENTION

This invention relates to transition metal poly(benzodithiolenes). In one of its more particular aspects, this invention relates to a process for producing transition metal poly(benzodithiolenes).

Metal dithiolenes are of significant interest in the fiel of solid state physics because of their stability at room temperature and in the atmosphere and because they exhibit a number of stable oxidation states containing open shell molecular orbitals. The latter are essential for achieving highly conducting systems. In addition, coordination complexes containing open shell molecular orbitals are potentially useful as organic ferromagnets and heterogeneous catalysts for hydrodesulfurization and coal liquification.

Maleonitrilodithiolato (mnt) complexes have been investigated, because they are readily prepared and the cyano substituents are sterically unencumbered, allowing a maximum intermolecular overlap. Highly conducting solids based on the nickel triad complexes of mnt:

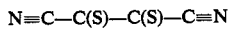

have been reported in J. A. McCleverty, *Progr. Inorg. Chem.*, 10:49 (1968). Complexes based on tetrathiafulvalenes have been disclosed by E. M. Engler et al., in "Molecular Metals", W. E. Hatfield, Ed., Plenum Press, N.Y., p. 31-34 (1979). Polymeric forms of such complexes have been a long sought goal. For example, in U.S. Pat. No. 4,111,857 poly(metal)tetrathiafulvalene tetrathiolate polymers having utility in antistatic agents and as conductive coatings are disclosed. None of the compositions previously known, however, displays the combination of chemical, physical, electrical and magnetic properties desired for many solid state physics applications.

It is accordingly an object of the present invention to provide polymeric compositions having desirable chemical, physical, electrical, and magnetic properties.

Another object of this invention is to provide solid compositions useful as conductive polymers, ferromagnetic and anti-ferromagnetic polymers, electrodes for fuel cells and heterogeneous catalysts.

Another object of this invention is to provide a facile method for preparing such compositions.

Other objects and advantages of the present invention will become apparent in the course of the following detailed description.

SUMMARY OF THE INVENTION

The compositions of the present invention are transition metal containing polymers based upon benzene-1,2,4,5-tetrathiol and its alkyl derivatives:

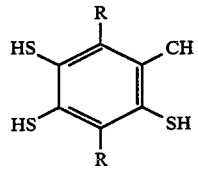

where R and R' are H or alkyl, such as $CH_3$ or $C_2H_5$ and may be the same or different. These polymers can be exemplified by the formula:

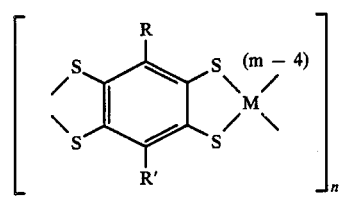

wherein R and R' are H or alkyl and may be the same or different, M is at least one transition metal, m is the valence of M and n is 2–1,000. These compositions are prepared by reacting benzene-1,2,4,5-tetrathiol with a transition metal salt. The polymers or oligomers prepared in accordance with this invention are insoluble, stable in air, paramagnetic, and display a conductivity in the range of about 0.2 to $10^{-4}$ S/cm.

DESCRIPTION OF THE PREFERRED EMBODIMENTS

The starting material, for example, benzene-1,2,4,5-tetrathiol, can be prepared by reacting 1,2,4,5-tetrachlorobenzene with an alkali metal isopropylmercaptide to form 1,2,4,5-tetrakis(isopropylthio)benzene. The tetraisopropyl derivative is then treated with a reducing agent, such as sodium, in a suitable organic base, such as pyridine, and methylated with a alkylating agent, such as methyl iodide, to produce 1,2,4,5-tetrakis(methylthio)benzene. Reduction to the desired benzene-1,2,4,5-tetrathiol by reaction with sodium in liquid ammonia, followed by acid hydrolysis completes the synthesis. This sequence of reactions is illustrated in Equations 1, 2, and 3 below:

(Equation 1)

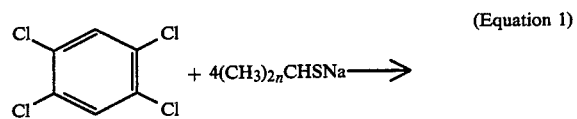

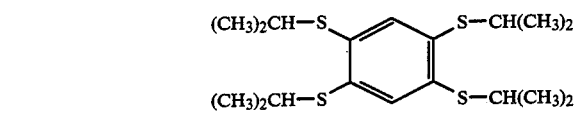

(Equation 2)

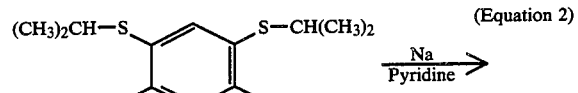

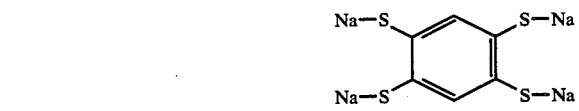

(Equation 3)

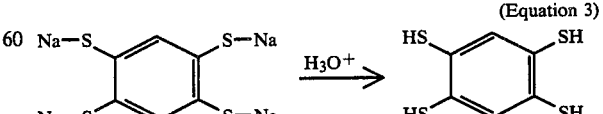

In a preferred embodiment, slightly more than 4 equivalents of mercaptide in HMPA are used. The preferred mercaptide is lithium isopropylmercaptide. The preferred solvent for the reduction is pyridine. Since benzene-1,2,4,5-tetrathiol is extremely sensitive to the atmosphere, it has been found desirable to store the tetrathiol in the protected form of the tetrakis(methylthio)benzene.

Alternatively, the corresponding tetrafluoro derivative can be directly methylated using an alkali metal methylmercaptide in the presence of a suitable solvent, such as N,N'-dimethylimidazolidinone (DMI) followed by reduction and acid hydrolysis. The conversion of 1,2,4,5-tetrafluorobenzene to 1,2,4,5-tetrakis(methylthio)benzene is shown in Equation 4.

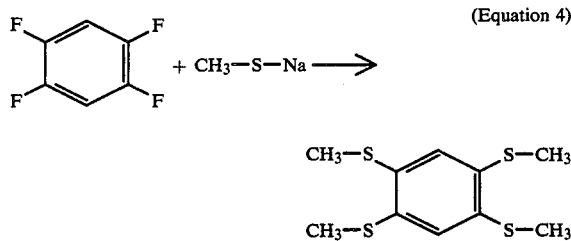

(Equation 4)

The above reaction is readily carried out at room temperature in DMI or HMPA. DMI is preferred for use as a solvent for this reaction, because separation of the product in HMPA is considerably more difficult requiring high pressure liquid chromatographic procedures or multiple crystallizations.

Removal of the protecting groups from the 1,2,4,5-tetrakis(methylthio)benzene to produce the desired benzene-1,2,4,5-tetrathiol is preferably carried out at the boiling point of ammonia in as high a dilution as possible in order to avoid undesired formation of the side product 1-methylthio-2,4,5-benzenetrithiol.

The product of Equation 3, benzene-1,2,4,5-tetrathiol is isolated as a white crystalline solid which is very soluble in most organic solids. It sublimes readily at temperatures above 80° C. at oil pump vacuum. Recrystallization is sometimes necessary to separate the desired tetrathiol from the monomethylthioether produced as a contaminating side product. For this purpose, recrystallization from a minimum amount of benzene is satisfactory.

The polymers of the present invention are prepared by reacting benzene-1,2,4,5-tetrathiol with any transition metal salt such as salts of titanium, Ti, vanadium, V, chromium, Cr, manganese, Mn, iron, Fe, cobalt, Co, nickel, Ni, copper, Cu, zinc, Zn, niobium, Nb, molybdenum, Mo, ruthenium, Ru, rhodium, Rh, palladium, Pd, silver, Ag, cadmium, Cd, tantalum, Ta, tungsten, W, rhenium, Re, osmium, Os, iridium, Ir, platinum, Pt, gold, Au and mercury, Hg. Of these, the iron, cobalt, and nickel salts are particularly preferred. Both $3d$ and $4d$ transition metal salts can be used. Reaction of the starting material with the metallic salts can be readily carried out in aqueous solution at reflux. Non-aqueous solvents such as organic bases can be used as well. For example, polar aprotic solvents can be used in conjunction with long chain tertiary amines. Neutral aqueous conditions are preferred.

The invention will be better understood by reference to the following examples, which are included for purposes of illustration and are not to be construed as limiting the scope of the present invention, which is defined in the claims appended hereto.

EXAMPLE 1

1,2,4,5-Tetrakis(isopropylthio)benzene

Into a 3 liter 3-neck flask equipped with a thermometer, magnetic stirring bar, nitrogen inlet and rubber septum with a needle connected through tubing to a mineral oil bubbler were added 500 ml of HMPA and 165 ml (1.78 moles) of isopropyl mercaptan. The content of the flask was then degassed by bubbling argon through the liquid for 15 minutes and the whole cooled to 10° C. with stirring. At this point, 159 ml of 10.2M n-Butyllithium (1.62 moles) was added slowly using a 15 gauge gas tight syringe and renewing the ice in the cooling bath as required. The reaction mixture was then heated to 60° C. while stirring and held at that temperature until butane evolution subsided. The reaction mixture was then cooled to 10° C. and 80 g (0.37 mole) of 1,2,4,5-tetrachlorobenzene was added. When addition was complete, the mixture was heated to 100° C. for 0.5 hour and monitored by thin layer chromatography (25:75 chloroform:hexane). Heating was continued until one single spot was observed.

To the resulting clear, orange-yellow reaction mixture was added slowly with stirring an excess of saturated aqueous NaCl solution until the product separated as a white solid, which was vacuum - filtered, dissolved in ether and extracted several times with water. The ether layer was dried and evaporated to yield 125 g of white crystals (90% based on tetrachlorobenzene), mp 77°–79° C.

EXAMPLE 2

1,2,4,5-Tetrakis(methylthio)benzene

Into a 3-neck 1 liter flask equipped with a thermometer, magnetic stirring bar, and gas inlet and outlet tubes was placed a solution of 25 g (66.72 millimoles) of the product of Example 1 in 300 ml of dry pyridine. The mixture was heated rapidly to 105°–110° C. and 8.29 g of Na pellets (360 millimoles) were added rapidly against a nitrogen flow. The reaction mixture was maintained below reflux but above 100° C. for 1 hour until all of the sodium had reacted. The mixture was then cooled to 10° C. and methyl iodide (24 ml) was added slowly by means of a syringe. The resulting mixture was stirred for 40 minutes and quenched with 350 ml of saturated aqueous NaCl. Water was then added to form a dilute suspension which was filtered under suction and washed copiously with water to yield a yellow, crystalline solid. The solid was washed with 150 ml of −10° C. methanol to yield 11.5 g (66%) of white product; mp:127°–129° C.

EXAMPLE 3

1,2,4,5-Tetrakis(methylthio)benzene From 1,2,4,5-Tetrafluorobenzene

Into a 3-neck flask equipped with a magnetic stirring bar, septum cap and gas inlet tube was placed 10.5 g (10.15 moles) of sodium methyl mercaptide and 100 ml of dry DMI. To the resulting suspension was added with stirring 3.75 g (2.79 ml, 0.025 mole) of 1,2,4,5-tetrafluorobenzene through the septum cap by means of a syringe. The reaction mixture was allowed to stand for 16 hours at room temperature and then monitored by tlc (silica gel, 3:1 hexane:ether). The chromatograph displayed only one spot. At this point the reaction mixture was added to 500 ml of water. A white perciptate formed which was filtered, washed copiously with water and sparingly with cold methanol to yield 6.17 g (94% yield) of white powder; mp 128°–130° C.

EXAMPLE 4

Benzene-1,2,4,5-tetrathiol

The product of Examples 2 and 3 (8 g, 30.5 millimoles) was weighed into a 1 liter 3-neck flask equipped with a dry-ice cold finger condenser, magnetic stirring bar and gas inlet and outlet tubes. Ammonia (600 ml) was distilled into the flask resulting in formation of a suspension. To this suspension was added 5.6 g (244 millimoles) of 2–4 mm sodium spheres. The cooling bath was removed and the ammonia was allowed to reflux for 4–8 hours. The reaction mixture was cooled to −78° C. (external), treated with an excess of $NH_4Cl$ and allowed to evaporate overnight under a positive pressure of nitrogen.

Next, thoroughly deaerated, 5% aqueous HCl (400 ml) was added via canula and after the inorganic solids dissolved, 500 ml of deaerated $CH_2Cl_2$ was added by canula to the resulting light grey suspension. The mixture was stirred until the aqueous layer became clearer and filtered through a Schlenk filter into a 1 liter Schlenk flask containing deaerated anhydrous $Na_2SO_4$. The dry $CH_2Cl_2$ solution was then Schlenk-filtered into another 1 liter Schlenk flask and the solvent removed in vacuo. The greyish white solid residue was transferred in a glove bag into a sublimer and sublimed at 80°–120° C. and 0.025–0.1 Torr to yield a white, crystalline product (5.1 g, 81% yield); mp, 145°–147° C. UV-VIS: ($CH_2Cl_2$, λmax (ε) 248 (31000), 270 sh, 320 (1900); ir (KBr) 2510, s; 1425, s; 1305, s; 1245, m; 1120, s; 1063, s; 915, m; 825, s; 605, w; 420, s. Nmr ($CDCl_3$, δ rel. to TMS) 3.68 s, 2H(S-H): 7.38 s, 1H. This compound is very atmosphere sensitive but can be stored in the solid state in a refrigerator within a dry box for several months.

EXAMPLE 5

Iron Poly(benzodithiolene)

A suspension of 246.3 mg of $FeCl_2$ in 9 ml of thoroughly degassed water was added via syringe to a refluxing suspension of 400 mg of the product of Example 4 in 25 ml of degassed water. The mixture turned dark rapidly, eventually turning black. The whole was allowed to reflux for 48 hours, cooled rapidly, filtered through a medium frit Schlenk filter, washed with water, with acetone and again with water and dried at 95° C. under vacuum for 12 hours.

Anal. Calcd. for $C_{75}H_{25}Fe_{14}S_{50}11H_2O$: C, 25.67; H, 1.34; Fe, 22.31; S, 45.64. Found: C, 25.74; H, 1.31; Fe, 22.02; S, 44.21.

EXAMPLE 6

Cobalt Poly(benzodithiolene)

The procedure of Example 5 was followed using $CoCl_2$ as the metal salt. Black microcrystals of a cobalt complex were isolated. The material had a conductivity of $10^{-3}$ S/cm.

Anal. Calcd. for $C_{66}H_{40}Co_2S_{44}$: C, 33.56; H, 1.71; Co, 4.99; S, 59.73. Found: C, 33.05; H, 1.93; Co, 4.94; S, 59.56.

EXAMPLE 7

The procedure of Example 5 was repeated using $NiCl_2$ as the transition metal salt. The polymer was found to have a conductivity of $2 \times 10^{-3}$ S/cm.

The polymers of this invention were found to display a room temperature compaction conductivity in the range of $0.2-10^{-4}$ S/cm and were found to be paramagnetic. Magnetic moments neff, were found to be 2.23 BM for the iron polymer, 2.69 BM for the cobalt polymer, and 0.83 BM for the nickel polymer.

Mossbauer spectroscopy of the iron poly(benzodithiolene) revealed three sets of doublets with quadrupole splittings of 0.65, 1.88, and 2.79 mm/sec in a ratio of 1:5:2 and isomer shifts of 0.35, 0.22, and 0.20 mm/sec, respectively. The isomer shifts (relative to $Fe^0$) suggested that all the iron was in the Fe+3 oxidation state in agreement with the magnetic susceptibility results. At 10° K., the Mossbauer spectrum showed no magnetic ordering. The different isomer shifts and quadrupole splittings are believed to result from iron in three different environments. The quadrupole splittings fall into the three typical areas of iron sulfur compounds. The splitting of 2.79 mm/sec is in the region seen for iron sulfur compounds in a strong square pyramidal crystal field. The splittings of 1.88 mm/sec is most characteristic of iron tris complexes of bidentate dithio ligands. The 0.65 mm/sec splitting implies a low field gradient at iron, characteristic of a relatively symmetric environment. Using a model in which the 1.88 splitting is assigned to a non-axially coordinated iron tris dithiolene site and the 0.65 splitting to a terminal iron dithiolene coordinated with one to two hydroxides and two to three water molecules, a number average molecular weight accounting for at least 11 iron atoms and 10 tetradentate ligands in a chain results. The molecules corresponding to these data are represented by the formula:

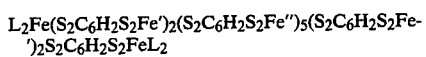

wherein L represents the benzodithiolene ligand forming the terminal groups of the polymer, and Fe, Fe', and Fe" refer to iron atoms in different coordination environments.

The above-described properties of the polymers of the present invention make them particularly adaptable for use as conducting polymers, ferromagnetic polymers and anti-ferromagnetic polymers. Because the transition metal atoms are readily oxidized and reduced to a number of stable oxidation states the polymers of this invention can be used as electrodes for fuel cells and in similar electrical applications. As suggested above, these polymers can contain repeating groups in which different metals provide the coordinating atoms. Such mixed metal polymers would have an imposed mixed valence making their utilization in catalysis practicable.

Although the present invention has been described in detail by reference to certain specific examples of polymeric compositions which can be prepared using certain specified reaction conditions, it should be apparent to one skilled in the art that various modifications are possible. For example, many mixed polymers and copolymers can be prepared within the scope of the present invention. It is intended, therefore, that this invention include such modifications and that the invention

What is claimed is:

1. A polymer of the formula:

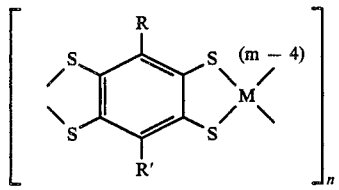

where R and R' are H or alkyl and are the same or different, M is at least one transition metal, m is the valence of M, (m-4) is the charge upon M, and n is 2–1,000.

2. A polymer according to claim 1 wherein each of R and R' is H.

3. A polymer according to claim 1 wherein M is a $3d$ transition metal.

4. A polymer according to claim 1 wherein M is a $4d$ transition metal.

5. A polymer according to claim 1 wherein M is Fe.

6. A polymer according to claim 1 wherein M is Co.

7. A polymer according to claim 1 wherein M is Ni.

8. A polymer according to claim 1 wherein M is more than one transition metal.

9. A polymer according to claim 1 wherein m is 2.

10. A polymer according to claim 1 wherein m is 3.

11. A polymer according to claim 1 wherein m is 4.

12. A polymer according to claim 1 which has a conductivity in the range of about 0.2 to $10^{-4}$ S/cm.

13. A process for preparing a polymer of the formula:

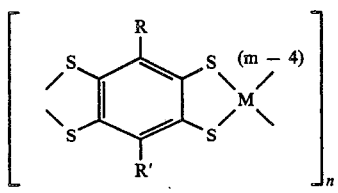

where R and R' are H or alky and are the same or different, M is at least one transition metal, m is the valence of M, (m-4) is the charge upon M, and n is 2–1,000, which comprises reacting a compound of the formula:

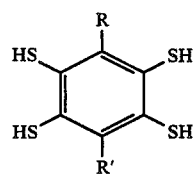

wherein R and R' are H or alkyl and are the same or different with a transition metal salt.

14. A process according to claim 13 wherein each of R and R' is H.

15. A process according to claim 13 wherein M is a $3d$ transition metal

16. A process according to claim 13 wherein M is a $4d$ transition metal.

17. A process according to claim 13 wherein M is Fe.

18. A process according to claim 13 wnerein M is Co.

19. A process according to claim 13 wherein M is Ni.

20. A process according to claim 13 wherein M is more than one transition metal.

21. A process according to claim 13 wherein m is 2.

22. A process according to claim 13 wherein m is 3.

23. A process according to claim 13 wherein m is 4.

24. A polymer of the formula
$L_2Fe(S_2C_6H_2S_2Fe')_2(S_2C_6H_2S_2Fe'')_5(S_2C_6H_2S_2Fe')_2S_2C_6H_2S_2FeL_2$, wherein L represents the benzodithiolene ligand forming the terminal groups of the polymer, Fe, Fe'0 and Fe" represent iron atoms in different coordination environments, and $C_6H_2$ is a tetravalent benzene radical.

* * * * *